US010809269B2

(12) United States Patent
Bardin et al.

(10) Patent No.: US 10,809,269 B2
(45) Date of Patent: Oct. 20, 2020

(54) USE OF SOLUBLE CD146 AS A BIOMARKER TO SELECT IN VITRO-FERTILIZED EMBRYO FOR IMPLANTATION IN A MAMMAL

(71) Applicants: UNIVERSITE D'AIX-MARSEILLE, Marseilles (FR); INSERM (INSTITUT NATIONAL DE LA SANTE ET DE LA RECHERCHE MEDICALE), Paris (FR); UNIVERSITE DE MONTPELLIER, Montpellier (FR); CENTRE HOSPITALIER UNIVERSITAIRE DE NIMES, Nimes (FR); ASSISTANCE PUBLIQUE HOPITAUX DE MARSEILLE, Marseilles (FR)

(72) Inventors: Nathalie Bardin, Marseilles (FR); Marcel Blot-Chabaud, Fuveau (FR); Sylvie Bouvier, Nimes (FR); Odile Lacroix, Aix-en-Provence (FR); Francoise Dignat-George, Marseilles (FR); Jean-Christophe Raymond Gris, Nimes (FR)

(73) Assignees: CENTRE HOSPITALIER UNIVERSITAIRE DE NIMES, Nimes (FR); INSERM (INSTITUT NATIONAL DE LA SANTE ET DE LA RECHERCHE MEDICALE), Paris (FR); UNIVERSITE D'AIX-MARSEILLE, Marseilles (FR); ASSISTANCE PUBLIQUE — HÔPITAUX DE MARSEILLE, Marseilles (FR)

( * ) Notice: Subject to any disclaimer, the term of this patent is extended or adjusted under 35 U.S.C. 154(b) by 251 days.

(21) Appl. No.: 15/568,097

(22) PCT Filed: Apr. 21, 2016

(86) PCT No.: PCT/EP2016/058825
§ 371 (c)(1),
(2) Date: Oct. 20, 2017

(87) PCT Pub. No.: WO2016/170021
PCT Pub. Date: Oct. 27, 2016

(65) Prior Publication Data
US 2018/0164323 A1    Jun. 14, 2018

(30) Foreign Application Priority Data
Apr. 21, 2015    (EP) .................................... 15305596

(51) Int. Cl.
*G01N 33/68* (2006.01)
*A61B 17/435* (2006.01)

(52) U.S. Cl.
CPC ......... *G01N 33/689* (2013.01); *A61B 17/435* (2013.01); *G01N 2333/70596* (2013.01); *G01N 2800/36* (2013.01)

(58) Field of Classification Search
CPC .... A61D 19/00–04; A61B 17/425–435; G01N 33/689; G01N 2333/70596; G01N 2800/36–368
See application file for complete search history.

(56) References Cited

U.S. PATENT DOCUMENTS

| | | | | |
|---|---|---|---|---|
| 2009/0298044 A1* | 12/2009 | Cecchi | ..................... | A01N 1/02 435/1.3 |
| 2011/0286963 A1* | 11/2011 | Blot-Chabaud | .... | C07K 16/3092 424/85.2 |
| 2013/0231263 A1* | 9/2013 | Hamamah | ............ | C12Q 1/6881 506/9 |

FOREIGN PATENT DOCUMENTS

| | | |
|---|---|---|
| EP | 1 944 611 | 7/2008 |
| FR | 2 795 820 | 1/2001 |

OTHER PUBLICATIONS

Kaspi, E. et al. "Soluble CD146 and APS: a potential biomarker of obstetrical complications?" *Lupus*, May 25, 2012, pp. 779-780, vol. 21, No. 7.

(Continued)

*Primary Examiner* — Thaddeus B Cox

(74) *Attorney, Agent, or Firm* — Saliwanchik, Lloyd & Eisenschenk

(57) ABSTRACT

The present invention relates to the field of human fertility treatment. The present invention more specifically relates to the identification of soluble CD146 (sCD146) as a biomarker which, when measured in an embryo culture medium, can be used to determine whether the embryo can be selected for implantation in the uterus of a mammal or not. The present invention thus provides a new tool and related kits to (pre)select embryo eligible for implantation. The invention also relates to methods for promoting pregnancy in a human who undergoes embryo transfer.

3 Claims, 6 Drawing Sheets

(56) References Cited

OTHER PUBLICATIONS

Figure 1:
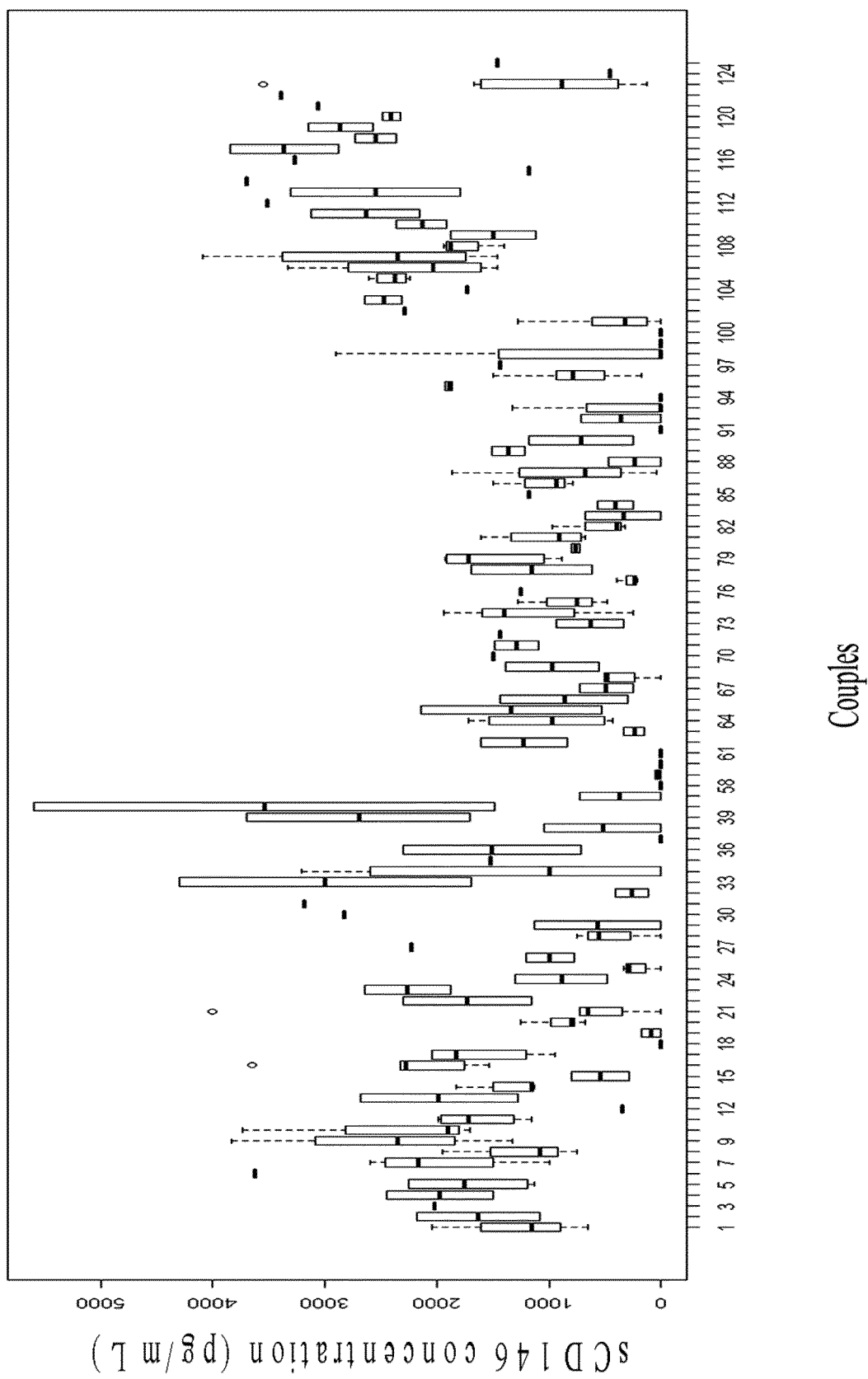

Kaspi, E. et al. "Identification of soluble CD146 as a regulator of trophoblast migration: potential role in placental vascular development" *Angiogenesis*, Apr. 1, 2013, pp. 329-342, vol. 16, No. 2.
Shih, I-E. "The Role of CD146 (Mel-CAM) in Biology and Pathology" *Journal of Pathology*, Sep. 1, 1999, pp. 4-11, vol. 189, No. 1.
Written Opinion in International Application No. PCT/EP2016/058825, dated May 31, 2016, pp. 1-5.
Cy-Quant™ Elisa sCD146, "Enzyme immunoassay of soluble CD146" BioCytex, Marseille, France, Version Apr. 2015, pp. 1-2.

\* cited by examiner

USE OF SOLUBLE CD146 AS A BIOMARKER TO SELECT IN VITRO-FERTILIZED EMBRYO FOR IMPLANTATION IN A MAMMAL

CROSS-REFERENCE TO RELATED APPLICATION

This application is the U.S. national stage application of International Patent Application No. PCT/EP2016/058825, filed Apr. 21, 2016.

FIELD OF THE INVENTION

The present invention relates to the field of human fertility treatment. Inventors indeed herein identify a new biomarker, soluble CD146 (sCD146), which, when measured in an embryo culture medium, can be used to determine whether the embryo can be selected for implantation in the uterus of a mammal or not. The present invention thus provides a new tool and related kits to (pre)select embryo eligible for implantation. The invention also relates to methods for promoting pregnancy in a human who undergoes embryo transfer.

BACKGROUND

Despite improvement of both embryo culture conditions and transfer techniques in in vitro fertilization (IVF) over the last decade, no significant improvement in pregnancy and delivery rates has been achieved (Kupka M S et al., Hum Reprod. 2014). More than 70% of embryos fail to implant. In this context, more than one embryo is transferred in order to enhance the chances of pregnancy. However, multiple embryos transfer induces a significant risk of multiple pregnancies that are known to provoke an increased fetal and maternal morbidity and mortality. To avoid this risk, single-embryo transfer has been advocated as a strategy to reduce the frequency of multiple births (McLernon et al., *BMJ.* 2010; Pandian Z et al., Cochrane Database Syst Rev. 2013). To date the evaluation of embryo quality is assessed morphologically with several criteria including cell size and symmetry, cell number, cleavage stage, anucleate cell fragments. However, embryo quality is not strictly correlated with embryo viability and implantation potential. Thus, a better assessment of the prognosis of implantation requires the search for biological markers of implantation in order to allow the transfer of one single embryo presenting a high implantation potential.

Membrane CD146 has been evidenced as expressed by embryo in early stages (Wang et al., Journal of Reproduction and Contraception, 2008) and recently inventors identified soluble CD146 as a new factor regulating embryo implantation in pregnant rat (Kaspi et al., Angiogenesis, 2013).

CD146 (or Ag S-Endo 1/MUC 18/M-CAM) is an adhesion molecule belonging to the immunoglobulin superfamily which is essentially localized in endothelial junction (Bardin et al. Blood 2001). Physiologically, CD146 is ubiquitously and constitutively expressed on human endothelium where it is involved in the cohesion of the endothelial monolayer. CD146 also exists as a soluble form generated by membrane proteolysis. Soluble CD146 (sCD146) was demonstrated to be present both in the supernatant of endothelial cells in culture and in normal and pathological human sera (Bardin et al. FEBS Lett 1998) (Bardin et al. Thromb Haemost 2003).

In obstetrics, membrane CD146 is expressed by the cumulus oocyte complex, the preimplantation embryo, the extravillous trophoblast and the endometrium (Wang et al. J Reprod Contracept 2008). In addition, the use of an anti-CD146 blocking antibody prevents implantation of the embryo in vitro and in vivo in mice. The AA 98 antibody, which blocks the membrane CD146 present on endometrial cells, prevents implantation of the blastocyst (Liu et al. J Cell Physiol, 2008). In pre-eclampsia, the expression of CD146 is greatly reduced or absent in connection with a decline in invasive capacity of these trophoblasts (Liu et al. Lab Investig J Tech Methods Pathol 2004). Concerning the soluble form, a decrease in serum sCD146 was described with gestational age during normal pregnancy (Kaspi et al. Angiogenesis 2013). In addition, inventors reported an elevated sCD146 in women with at least two unexplained fetal loss as compared to women with at least one living child (Pasquier et al. Thromb Haemost 2005). They also reported different effects of sCD146 on extravillous trophoblasts: i) in vitro, where it inhibits migration, proliferation and pseudocapillary formation of extravillous trophoblastic cell line, HTR/Svneo cells, ii) in ex vivo, placental explants, where it decreases invasive potential and iii) finally, in a model of pregnant rat, where repeated injections of sCD146 decrease the pregnancy rate and the number of embryos per litter. Placental histological studies of the placenta of these rates show that these effects are accompanied by a decrease in the migration of glycogen cells, which are similar to extravillous trophoblasts in women (Kaspi et al. Angiogenesis 2013).

SUMMARY OF THE INVENTION

Inventors herein reveal the presence of soluble CD146 protein (sCD146) in embryo culture media thanks to ELISA and western blot experiments. They demonstrate that sCD146, when measured in an embryo culture medium, can be advantageously used as a biomarker for disqualifying for in utero implantation an embryo associated to a high-risk of implantation failure, for identifying an implantable embryo, or for selecting, among several, the embryo associated to the greatest implantation potential.

A first object herein described thus relates to the use of the soluble CD146 protein (sCD146) present in an embryo culture medium as a biomarker of implantation of said embryo in the uterus of a mammal.

Herein described is also an early and non-invasive method for obtaining useful information about an embryo obtained by in vitro-fertilization (IVF), in particular for evaluating/determining the implantation potential of an in vitro-fertilized embryo, typically for identifying embryo with an implantation potential ("implantable embryo"), when transferred in the uterus of a mammal. Such a method is typically implemented to disqualify, or on the contrary select, for example preselect, embryo for implantation in the uterus of a mammal.

The method of the invention advantageously comprises an in vitro step of measuring sCD146 in the embryo culture medium, preferably in the embryo culture medium supernatant, and a step of comparing the measured value to a threshold value.

Herein described are also a kit comprising a detectable monoclonal antibody binding sCD146, as well as uses of such a kit for identifying among embryos obtained by in vitro fertilization (IVF) those eligible for implantation in the uterus of a mammal, preferably for selecting the embryo associated to the greatest implantation potential, or for checking the implantation status ("implantability") of a single embryo.

Also described is a method for promoting pregnancy in a human who undergoes embryo transfer comprising an in vitro step of measuring sCD146 in the embryo culture medium and a step of comparing the measured value to a threshold value.

DETAILED DESCRIPTION OF THE INVENTION

The present description relates to the use of the soluble CD146 protein (sCD146) present in an embryo culture medium as a biomarker of implantation of said embryo in the uterus of a mammal, typically of a human being.

sCD146 is an innovative tool representing an early and non-invasive biomarker. Thanks to the present invention, the selection of embryos eligible for transfer into the uterus of a mammal does no longer rely only on embryo morphological criteria. sCD146 can be tested in any embryo culture medium whatever the quality of the embryo as defined by Istanbul classification ("top", "fair" or "poor" quality). The selection can in addition be performed very early in the embryo development and earlier than with existing techniques. sCD146 can indeed be detected in the embryo culture medium at the early stage of the embryo development, typically as early as two days following in vitro oocyte fertilization.

The herein described new biomarker advantageously allows the transfer of a single embryo, typically of the embryo presenting, among several, the greatest potential of implantation in the uterus of a mammal. This option may be taken to avoid the risk of multiple pregnancies and the related complications in the context of IVF [classical IVF or intra-cytoplasmic sperm injection-IVF (ICSI-IVF)] and at the same time to significantly enhance the chances of pregnancy while reducing the costs associated to IVF procedure.

The description also provides a method for obtaining useful information about an embryo obtained by in vitro-fertilization (IVF), in particular for evaluating/determining the implantation potential of an in vitro-fertilized embryo, preferably for identifying/selecting embryo with an implantation potential ("implantable embryo"), when transferred in the uterus of a mammal. Such a method is typically used to disqualify, or on the contrary to select, for example preselect, in vitro-fertilized embryo for implantation in the uterus of a mammal.

The method of the invention is advantageously non-invasive and comprises an in vitro step of measuring sCD146 in the embryo culture medium, typically in the embryo culture medium supernatant, and a step of comparing the measured value to a threshold value. When embryos are preselected thanks to the method of the invention, this method can further comprise a subsequent step of morphological selection consisting in examining the embryo using criteria of acknowledged value according to the skilled person such as cell size and symmetry, cell number, cleavage stage, presence of anucleate cell fragments.

A medium to be employed may be any of conventional media conventionally used in embryo culture or transfer. The culture medium is typically an artificial culture medium which basically contains glucose, pyruvate, and energy-providing components as well as factors released by the preimplantation embryo which develops therein. The media can further comprise for example amino acids, nucleotides, vitamins, and cholesterol.

A serum-free medium is preferred considering that the risk of contamination with prion or other infectious agents should be eliminated.

The culture medium is regularly renewed. The medium can be the same all along the culture period or changed over the culture period depending on the development stage.

An example of appropriate media is the GLOBAL® (Life Global) supplemented with 10% Human Serum Albumin. Such a media can be used suitably in the culture to be continued until blastocysts are formed at Day 5.

The culture medium, or supernatant of the culture medium, to be collected is preferably that in which at least 1 day of embryo culture was performed before collection. Considering both the necessity of supplying a sufficient amount of a medium to embryos and the convenience for collecting the embryos from the medium, the above-mentioned culture of human embryos is conducted preferably in an amount of the medium which corresponds to 50 µL-1 mL of the medium per human embryo, and more preferably to 500-800 µL, typically 600 of the medium per human embryo.

The collected culture medium or culture supernatant may be tested directly, or frozen-stored and thawed before being tested. It is also allowed to add one or more pharmaceutically inert diluents (e.g., sterile purified water, or aqueous solution containing human plasma albumin, glucose, sodium chloride and the like, which are compounds contained in GLOBAL®) to increase the volume by dilution into a volume which is easier to handle, e.g., 0.2 mL or 0.5 mL.

A particular method herein described is a method for obtaining useful information about an embryo obtained by in vitro-fertilization (IVF), and preferably determining using said information whether the embryo can be selected for implantation in the uterus of a mammal. This method comprises an in vitro step of measuring sCD146 in the embryo culture medium and a step of comparing the measured value to a threshold value. The presence in the embryo culture medium of sCD146 in a quantity above a threshold value, is indicative for (associated with) a high-risk of embryo implantation failure in the uterus of a mammal, and the presence of sCD146 in a quantity equal to or below said threshold value is indicative for (associated with) a chance of embryo implantation success in the uterus of a mammal. The lowest the sCD146 concentration the highest the chance of embryo implantation success. The "threshold value" may vary depending on the nature of the media used for culture and on the part of the media which is concretely tested (supernatant or total medium). For example, when the measurement of sCD146 is performed on the culture medium supernatant using Global® medium (Life Global) such as performed in the experimental section, the threshold value is of 1164 pg per ml of supernatant.

The measuring step is advantageously performed between two and five days following oocyte fertilization, preferably two days following oocyte fertilization, typically at the day of the embryo transfer into the uterus of a mammal.

A Kit, typically an in vitro-fertilized embryo selection kit, comprising a detectable antibody binding sCD146, preferably a detectable monoclonal antibody binding sCD146, is also herein described as well as its use for determining whether an embryo obtained by in vitro fertilization (IVF) can be selected for implantation into the uterus of a mammal.

A particular kit comprises a detectable antibody binding sCD146, preferably a detectable monoclonal antibody binding sCD146, optionally together with an appropriate substrate revealing said detectable antibody when bound to sCD146 in an embryo culture medium, preferably a detectable (monoclonal) antibody which selectively binds the soluble form of CD146 and does not bind a CD146 membrane-bound form. The kit optionally further comprises a pharmaceutically inert diluent deprived of sCD146 to be used to prepare a control, or at least one solution comprising a known concentration of sCD146, preferably several solutions (such as 2, 3, 4, 5 or 6 solutions) having different known concentration of sCD146s, together with a calibration curve (typically from 0 pg/ml to 10 000 pg/ml). Generally, the kit also comprises one or more containers filled with one or more of the substances (antibody, diluent, and solutions) herein disclosed. Associated with such container(s), a labelling notice may be added providing instructions for using the substances according to the disclosed methods.

The antibody binding sCD146 can be synthetic, monoclonal, or polyclonal and can be made by techniques well known in the art.

A monoclonal antibody binding sCD146 is advantageously selected from clone COM 3D9, clone COM 2F6, clone COM 5G6, clone COM 7A4 and clone F4-35H7 (S-endo 1) from BioCytex, and is preferably clone COM 7A4.

Methods of making such antibodies are known in the art (See for example Despoix N, Walzer T, Jouve N, Blot-Chabaud M, Bardin N, Paul P, Lyonnet L, Vivier E, Dignat-George F, Vély F. Mouse CD146/MCAM is a marker of natural killer cell maturation. Eur J Immunol. 2008; 38: 2855-64).

The detectable monoclonal antibody binding sCD146 of the kit is preferably in a concentrated dosage form in order to detect low concentrations of sCD146 in the embryo culture medium or supernatant. A concentrated antibody is therefore preferably used. In a preferred embodiment, the concentrated antibody allows the detection of sCD146 in the supernatant of an embryo medium containing no more than 100 ng/ml, preferably no more than 50 ng/ml, even more preferably no more than 10 ng/ml, of sCD146.

The determination of the presence as well as the measure of the quantities of sCD146, is preferably determined in an immunoassay through a one-step method wherein the culture medium, or culture supernatant, is directly contacted with the appropriate antigen or through a method implying a preliminary treatment of the biological sample. The immunoassay can be performed through well-known methods of the art: in solid phase or homogeneous phase, in one or two steps, through competitive method, etc.

More preferably, said immunoassay is selected from the group consisting of ELISA, FEIA, western blot, dot blot, bead-based assay, antigen array and Radio Immuno Assay.

In an ELISA, an antigen must be immobilized to a solid surface and then complexed with an antibody that is linked to an enzyme. Detection is accomplished by assessing the conjugated enzyme activity via incubation with a substrate to produce a colored product.

In FEIA, the colored product is fluorescent.

In Radio Immuno Assay, the final product is radioactive.

Protein detection using the dot blot protocol is similar to western blotting in that both methods allow for the identification and analysis of proteins of interest. Dot blot methodology differs from traditional western blot techniques by not separating protein samples using electrophoresis. Sample proteins are instead spotted onto membranes and hybridized with an antibody probe.

Semi-quantitative measurements can be obtained with each of the previously described methods using for example normal controls to normalize the value and then establish a ratio, or using a positive control as a calibrator (expressed in arbitrary units).

The detection may be performed on a solid support, for example a microplaque, on which is laid out the antigen corresponding to sCD146, to be detected and quantified, or solid particles, test tubes, etc.

Antibodies recognizing sCD146 usable in the context of the present invention are preferably labelled with one or more tags (detection marker) allowing for their identification, follow-up, detection and/or measurement. Detection markers may be selected for example from a fluorophore, a magnetic bead, an antigenic epitope, a substrate of a specific enzyme, a binding domain of a specific ligand, and any other molecule or moiety which may be detected or quantified. Antibodies usable in the context of the present invention may also be anti-antibodies used to identify, follow-up, detect and/or measure the antibodies that recognize the sCD146.

The pharmaceutically inert diluent deprived of sCD146 may be selected for example from sterile purified water, or aqueous solution containing human plasma albumin, glucose, sodium chloride and the like such as the GLOBAL® medium.

Also described is a method for promoting pregnancy (i.e. increasing the success rate of achieving pregnancy) in a mammal, typically in a human being, who undergoes embryo transfer comprising an in vitro step i) of measuring sCD146 in the embryo culture medium, a step ii) of comparing the measured value to a threshold value according to the invention and deciding that the embryo is eligible for implantation in the uterus of mammal if the measured value is equal to or below the threshold value and that the embryo is not eligible for implantation in the uterus of mammal if the measured value is above the threshold value, optionally a step iii) of examining the embryo using morphological criteria, and a step iv) of transferring the embryo in the uterus of the mammal if the measured value is equal to or below the threshold value and if said embryo satisfies morphological criteria of implantation.

In the previously described method optional step iii) can be performed first, i.e. before steps i) and ii). Step iii) can in another embodiment be performed between steps i) and ii).

Further aspects and advantages of the present invention will be described in the following examples which are given for purposes of illustration and not by way of limitation.

LEGEND TO THE FIGURES

FIG. 1: Distribution of couples and embryos.

Figure 2:
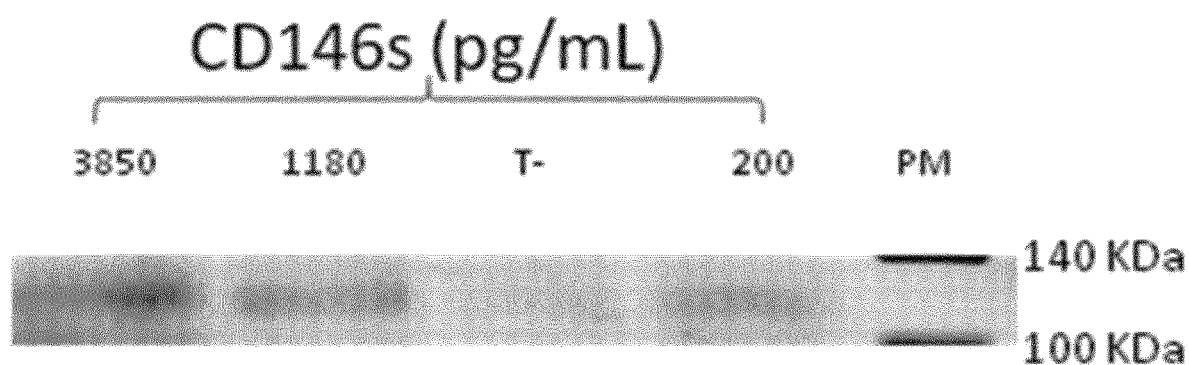

FIG. 2: Western blot analysis of positive or negative embryos supernatants by ELISA test.

Negative control corresponds to culture medium without any embryo. MW, molecular weight.

Figure 3:
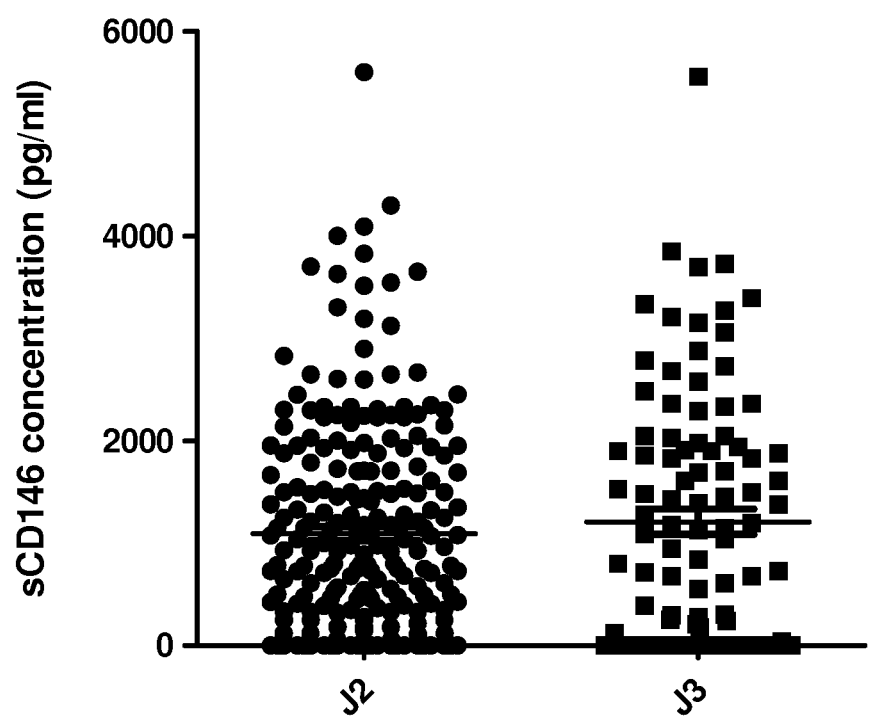

FIG. 3: sCD146 concentrations at day 2 (D2) and day 3 (D3).

Figure 4:
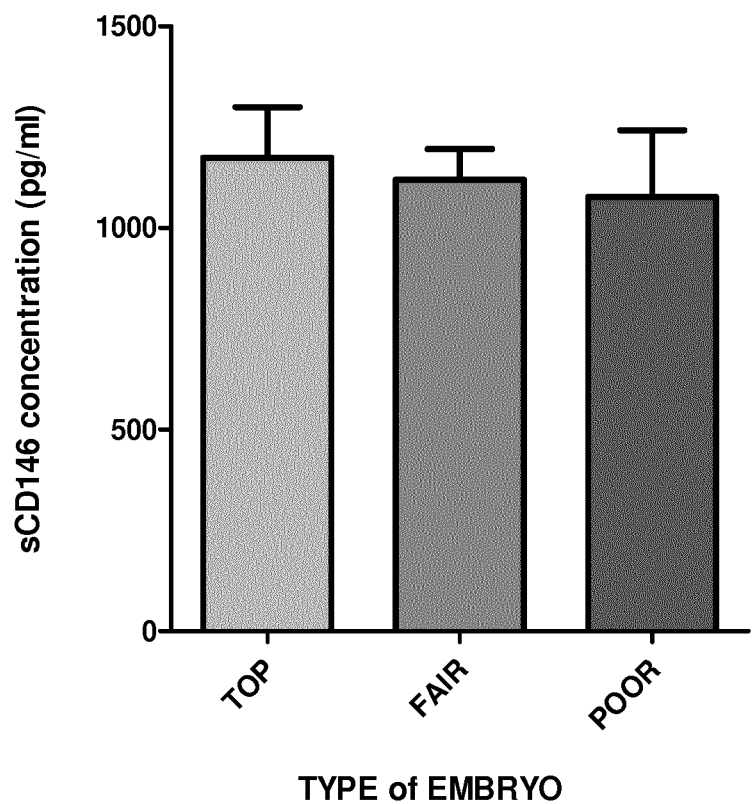

FIG. 4: sCD146 concentrations according to the embryo quality as defined by the classification of Istanbul (type 1 "top" n=90, type 2 "fair" n=190, or type 3 "poor" n=43).

Figure 5:
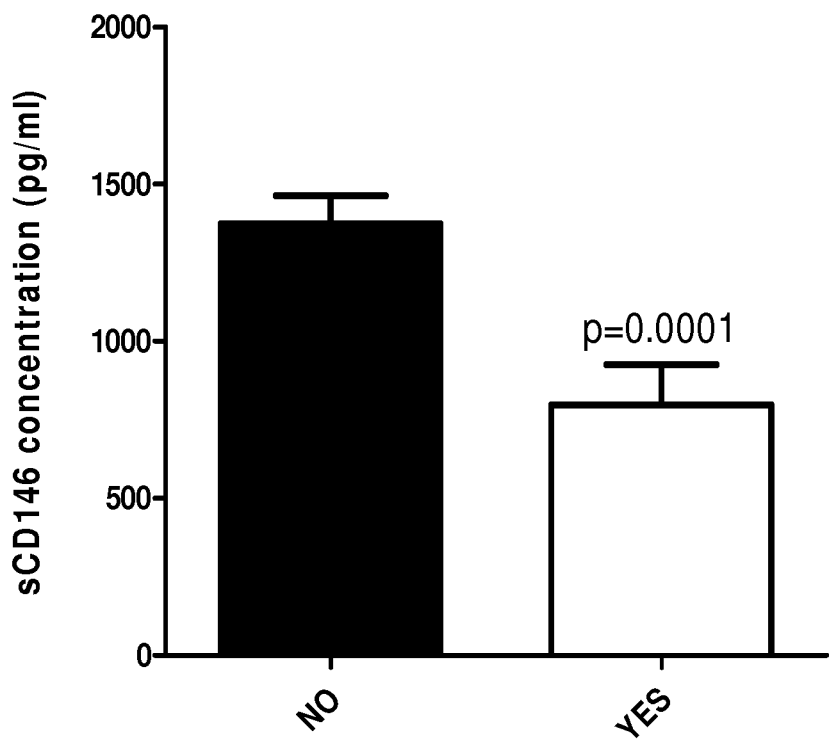

FIG. 5: Comparison of sCD146 concentrations between implanted (YES, n=63) and non-implanted embryos (NO, n=172).

Figure 6:
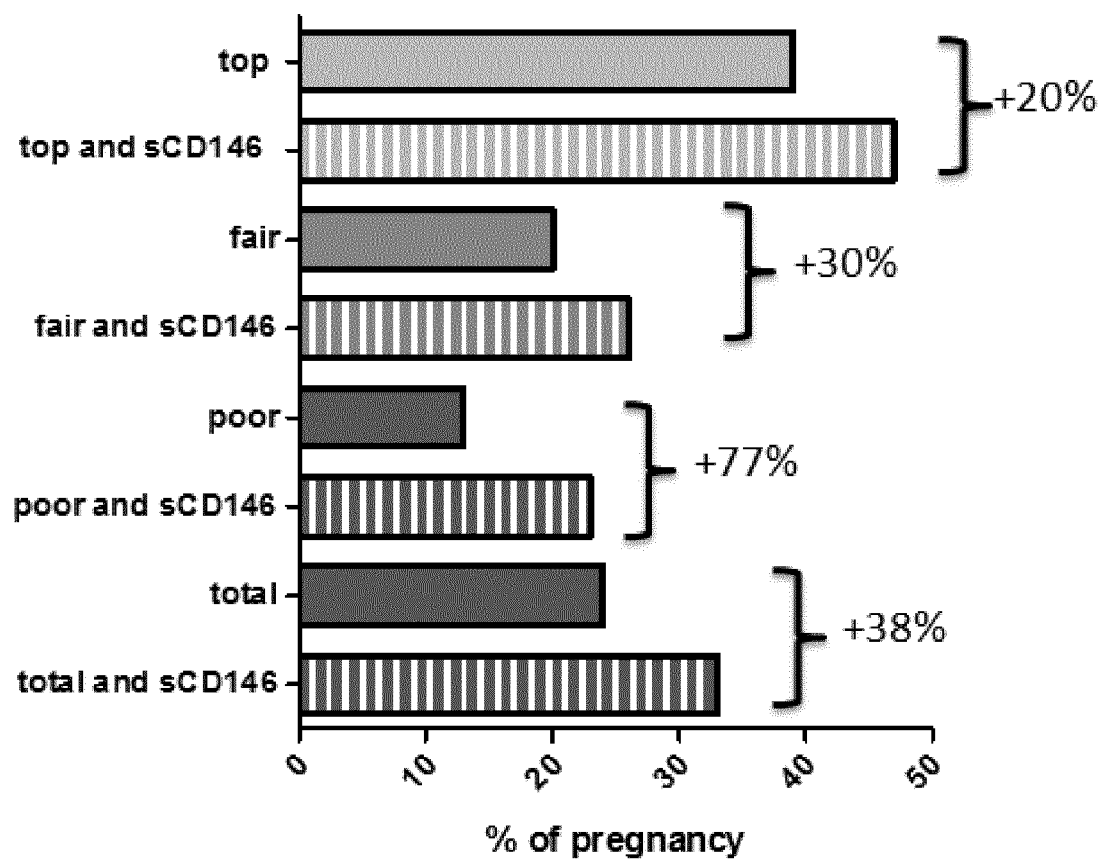

FIG. 6: Percentage of pregnancy according to the value of sCD146.

EXAMPLES

Material and Methods

Patients

From March 2013 to December 2014, inventors performed an initial pilot study on 162 couples who underwent In Vitro Fertilization (IVF) attempts in the reproductive department of medical center at La Conception University Hospital (AP-HM, Marseille, France). All couples were informed that embryo culture media from transferred embryos would be preserved after embryo transfer for research purposes, and chose to participate or not to this study. Each couple was included once only. Inventors excluded from this study oocyte and sperm donors and patients with lack of consent. The Institutional Review Board approved this investigation.

Treatment Protocol

Patients underwent a controlled ovarian hyperstimulation using three types of protocols: long agonist protocol (GnRH agonist administration in the luteal phase of the previous cycle); short agonist protocol (daily GnRH agonist administration since the first day of the IVF cycle); and antagonist protocol (daily GnRH antagonist administration from Day 5). Recombinant FSH and/or hMG were used at doses ranging between 150 IU/day and 450 IU/day, in accordance with body mass index, woman's age, basal day 3 FSH value and number of antral follicles. Patients routinely underwent serial transvaginal ultrasound starting on Day 8 of ovarian hyperstimulation and serum estradiol (E2) measurements. The dose of gonadotropin was then adjusted according to the ovarian response. Ovulation triggering was performed with subcutaneous injection of recombinant human Chorionic Gonadotrophin (hCG, Ovitrelle®, Merck-Serono, 250 μg) when at least three follicles reached a mean diameter of 16 mm. Oocyte retrieval was carried out under local or general anesthesia using transvaginal ultrasound-guided puncture of follicles 35 hours after hCG administration. Conventional IVF or IntraCytoplasmic Sperm Injection (ICSI-IVF) was then carried out according to sperm parameters, using routine protocols. After assessment of normal fertilization (i.e. fertilized oocytes with two pronuclei, so-called diploid zygotes) 18 h post-insemination, zygotes were then individually cultured at 37° C., 5% $CO_2$ in 500 μl of Global® medium (Life Global) until the day of embryo transfer (Day 2 or 3).

They were observed 26 hours post-insemination in order to detect the early cell-cleavage. Obtained diploid embryos were graded before transfer according to scoring system based on cell size and symmetry, fragmentation and cell number according to Consensus of Istanbul (Alpha Scientists in Reproductive Medicine and ESHRE Special Interest Group of Embryology. Hum Reprod. 2011).

Embryos were then classified in 3 subgroups:

1/ Top quality embryos with equally sized cells, no fragmentation or less than 10%, and 4 cells on day 2 or 8 cells on day 3; preferentially selected for transfer when available;

2/ fair quality embryos with stage-specific cell size for majority of cells and/or 10-25% fragmentation, and/or 3 or 5 cells on Day 2 or 6, 7 or 9 cells on day 3;

3/ Poor quality embryo with no stage specific cell size and/or severe fragmentation (>25%) and/or 2 cells or >5 cells on Day 2 or <6 or >9 cells on day 3.

After embryo transfer, luteal phase was then supported by daily progesterone tablets (DuphastonR 30 mg/day; Abbot Products SAS, France). Pregnancies were diagnosed by serum positive hCG levels (>100 IU/l) 14 days after embryo transfer. Clinical pregnancies were confirmed by the presence of a gestational sac with cardiac activity on vaginal ultrasound examination during the 5th week after embryo transfer.

Embryo Supernatants

Culture media (500 μl Global®) of each transferred embryo were collected individually after embryo transfer, frozen and stored at −20° C. until sCD146 quantification. Collecting embryos supernatants is a non-invasive technique; there was no change in the care of patients. IVF outcomes were retrospectively compared in all patients.

Confirmation of the Presence of sCD146 in Embryo Supernatants

CD146 has already been identified in early stages of human embryo (Wang H et al. J of Reprod and contracept 2008) and it is known that a soluble form can be generated by shedding of membrane CD146 in trophoblastic cells (Kaspi et al., Angiogenesis, 2013). However, no data is available on secretion of sCD146 by embryos in the literature. Inventors carried out western blot analysis on embryo supernatant to confirm the release of sCD146 by embryos. 50 μL of embryo supernatants or negative control (culture medium) were submitted to 4-12% NuPage SDS-polyacrylamide gel electrophoresis (In Vitrogen/Life Technologies, USA) and transferred onto nitrocellulose membrane. Bio-Rad molecular weight markers were used. Transfer was performed at constant voltage (60 V) for 2 hours. After blocking with 4% Bovine Serum Albumine (BSA) in TBS-Tween 20 (TBST), soluble CD146 was evidenced with anti-human CD146 antibody (7A4 1 mg/l, Biocytex, Marseille, France) diluted in TBST (1:3000), overnight at 4° C. with constant shaking. Soluble CD146 was revealed by HRP-coupled goat anti-mouse antibody (Thermo Scientific, USA). Membranes were scanned and analyzed by the G:Box-Chemi-XT4 (Syngene, Cambridge, United Kingdom).

Soluble CD146 Assay sCD146 was assayed using an adaptation of the commercial ELISA assay (CY-QUANT sCD146, Biocytex, Marseille). Plates were coated with specific mouse monoclonal anti-human CD146 F(ab')2 fragments. 200 μL of embryo supernatant ½ diluted was added to each well and incubated for 30 minutes at room temperature. After incubation, the plates were washed five times, followed by incubation with a specific HRP-coupled anti-CD146 monoclonal antibody (7A4-HRP, 1 mg/ml, Biocytex, Marseille, France) at a 1:1 000 dilution in a specific diluent for 30 minutes at room temperature and then washed five times. 200 of tetramethylbenzidine (TMB) substrate was incubated for approximately 20 minutes at room temperature. The colorimetric reaction was then stopped by the addition of 100 μL of an acid solution. The intensity of the signal was directly related to the concentration of sCD146 initially contained in the sample. Adaptation of the technique was based on the substitution of the diluent of the kit by embryo culture medium, conserved in the same conditions as embryo supernatants (37° C., 5% $CO_2$ for 48 h), but without embryo in order to improve repeatability and reproducibility of the test. A concentrated anti-CD146 antibody was also used because of lower concentration of sCD146 in supernatants than in human serum or plasma (7A4-HRP, 1 mg/ml, Biocytex, Marseille, France). Concentrations of sCD146 in the embryo supernatants were determined using a calibration curve of solutions with known concentrations of sCD146 (from 0 pg/ml to 10 000 pg/ml). Due to the low volume of supernatants and the supplier's recommendations (200 µl/well), each sample was diluted (1:2) and analyzed in simplicate. Optical density (OD) was measured at 450 nm.

A repeatability and reproducibility analysis was performed and data showed 4% of repeatability and 11% of reproducibility (n=3 tests).

Collected Data

Inventors collected patient's clinical and biological data (age, body mass index, smoking habit, indication and duration of infertility, assessment of ovarian reserve evaluated by antral follicles count and basal Day 3 FSH and AMH plasma levels), characteristics of the IVF cycle and laboratory data (number of previous IVF-ICSI attempts, conventional IVF or ICSI-IVF, ovarian stimulation protocol, estradiol levels and endometrial thickness on the triggering day, number of retrieved oocytes, of mature oocytes, of diploid embryos obtained and of embryo transferred, morphologic score of embryos transferred, the day of transfer), and occurrence of clinical pregnancies.

Statistical Analysis

Data were expressed as mean±SEM. Statistical analysis was performed with the Prism software (GraphPad Software Inc., San Diego). Significant differences were determined using non parametric Mann Whitney and Chi2 tests. Because we have several observations for each couple, a generalized estimating equation (GEE) with a multivariate model is used. A p-value<0.05 was considered significant.

Results

Baseline Patient Characteristics

The study group included 162 couples who underwent IVF or IVF-ICSI with at least one transferred embryo. Of the 1 505 retrieved oocytes, 1 199 were mature (81.2%), 907 embryos were obtained and 738 were diploid. On day 2/3, a total of 261 embryos were transferred, with one or two embryos per transfer. Out of the 162 couples studied, complete data (sCD146 test result and pregnancy testing) were available for 138 of them with 225 transferred embryos (FIG. 1). These 225 transferred embryos resulted in 36 clinical pregnancies and included 33 singletons and 3 twins. 146 embryos were transferred at day 2 (D2, 64.8%), 79 at day 3 (D3, 35.2%). The mean number of embryos transferred was 1.63 (SD+/−0.53) and the implantation rate was 17.3% (39 sacs/225 embryos). The overall pregnancy rate was 26.1% (36 pregnancies/138 patients).

Among these 225 embryos, and according to Istanbul classification, 64 were "top quality embryos", 125 "fair quality" and 36 "poor quality". Their implantation rate was of 26.2%, 12% and 5.7% respectively.

Women's mean age was 33.1 years (SD+/−4.51). Controlled ovarian hyperstimulation was performed using short agonist protocol in 21.5% of attempts, long agonist protocol in 58.3% and antagonist protocol in 20.2%. 54% of the couples underwent classical in vitro fertilization, 46% intracytoplasmic sperm injection. The mean row of IVF cycles was 1.77 (SD+/−0.97). Indications for IVF were related to male infertility for 58% of couples or to female infertility for 42%. Characteristics of the studied population (ovarian reserve status, clinical prognosis factors of implantation, ovarian response and endometrial status on the triggering day) are summarized in Table 1.

TABLE 1

Characteristics of the studied population.
Data are expressed as mean +/− SD and median [IQR]

| | |
|---|---|
| AMH (ng/mL) | 3.68 +/− 3.38 |
| | 2.50 [1.36-5.20] |
| FSH (UI/L) | 7.452 +/− 2.601 |
| | 7 [5.6-8.78] |
| Antral follicles count | 14.32 +/− 8.74 |
| | 12 [9-18] |
| Body mass index (BMI, Kg/m$^{-2}$) | 23.81 +/− 4.98 |
| | 22.5 [20.7-26.0] |
| Current smokers (%) | 28 |
| History of previous pregnancy (%) | 35 |
| Estradiol (pg/mL) on the triggering day | 2394 +/− 1392 |
| | 2216 [1495-2946] |
| Endometrial thickness on the triggering day | |
| Good quality: 8-13 mm (%) | 74 |
| Poor quality: <8 mm or >13 mm (%) | 24 |

Presence of sCD146 in Embryo Supernatants from Day 2

To confirm the presence of sCD146 in embryos supernatants, inventors performed a western blot analysis on 4 samples with various sCD146 concentration: the first one was evaluated, by ELISA, at 220 pg/ml (transferred at day 2), the second at 1 178 pg/ml (transferred at day 2), the third at 3 850 pg/ml (transferred at day 3) and the last one was the negative control and corresponded to the diluent used for the assay (embryo culture medium, conserved in the same conditions as embryo supernatants but without embryo) (FIG. 2).

Since embryos were transferred at day 2 (D2) or 3 (D3), inventors compared sCD146 concentrations in embryo supernatants at D2 and D3. No significant difference in sCD146 concentrations between D2 or D3 transfers was shown (p=0.36) (FIG. 3).

sCD146 Concentrations and Embryo Quality In practice, embryo selection is based on its morphology. This is the only criterion assessed before transfer. Thereby, inventors studied relationship between concentrations of sCD146 and embryo quality as defined by Istanbul classification. They found that the concentrations of sCD146 did not correlate with the type of embryo (FIG. 4).

sCD146 Concentrations and IVF Outcome

Inventors found a significant difference in sCD146 concentrations between embryos with and without implantation (FIG. 5) with a low concentration associated with high implantation potential. After stepwise multivariable analysis with adjustment to co-variables Istanbul classification and FSH rate, they confirmed the significant association between a low sCD146 concentration and implantation with a Wald chi-square at 5.39 (p=0.02).

Efficacy of sCD146 as a Biomarker of Implantation

The ROC curve computed showed that the optimal sensitivity (71%) and specificity (60%) for implantation was found at 1164 pg/mL sCD146. At this threshold, the percentage of pregnancy was increased by about 40%. This augmentation is maintained into the three Istanbul groups with an augmentation of 20, 30 and 77% in top, fair and poor embryo quality, respectively (FIG. 6).

Conclusions

To avoid the risk of multiple pregnancies and the related complications, it is necessary to select only one embryo to transfer. The prediction of the implantation potential of embryos thus constitutes an imperative in IVF. In this experiment, inventors showed that sCD146 represents an early, noninvasive and innovative biomarker to select the embryo with the highest implantation potential. Interestingly this biomarker is independent of the morphology criteria as defined by Istanbul classification which were up to now the only criteria of selection. Thus the embryo selection with sCD146 can be useful whatever the group of embryos. Therefore sCD146 represents the first biomarker of the embryo selection that improves the accuracy of embryo selection and the effectiveness of IVF.

An early, precise and accurate choice of the embryo with the best potential for implantation indeed constitutes the best strategy to enhance the chances of pregnancy in IVF.

Inventor evidenced in their experiments the presence of sCD146 in embryos supernatants both by ELISA and western blot. This detection could be achieved as soon as day 2 in embryo supernatant. These results bring out sCD146 as an advantageous biomarker in IVF since until now no biomarker could be detected in the blastocyste early stage. Moreover sCD146 use displays another advantage since majority of centers transferred embryos on day 2 or 3, a period which is compatible with sCD146 detection. Finally early detection of sCD146 is also associated with cost reduction.

sCD146 concentration in embryo supernatants represents an early, noninvasive and innovative biomarker to select the embryo with the highest implantation potential. This biomarker advantageously improves the effectiveness of IVF by reducing the time and cost to obtain a pregnancy.

REFERENCES

Alpha Scientists in Reproductive Medicine and ESHRE Special Interest Group of Embryology. The Istanbul consensus workshop on embryo assessment: proceedings of an expert meeting. Hum Reprod. 2011; 26:1270-1283.
Bardin et al. FEBS Lett 1998.
Bardin et al. Blood 2001.
Bardin et al. Thromb Haemost 2003.
Kaspi et al., Angiogenesis, 2013.
Kupka M S, Ferraretti A P, de Mouzon J, Erb K, D'Hooghe T, Castilla J A, Calhaz-Jorge C, Assisted reproductive technology in Europe, 2010: results generated from European registers by ESHRE. Reproduction and Embryology. Hum Reprod. 2014; 29:2099-113.
Liu et al. J Cell Physiol, 2008.
Liu et al. Lab Investig J Tech Methods Pathol 2004.
McLernon D J, Harrild K, Bergh C, Davies M J, de Neubourg D, Dumoulin J C, Gerris J, Kremer J A, Martikainen H, Mol B W, Norman R J, Thurin-Kjellberg A, Tiitinen A, van Montfoort A P, van Peperstraten A M, Van Royen E, Bhattacharya S. Clinical effectiveness of elective single versus double embryo transfer: meta-analysis of individual patient data from randomised trials. BMJ. 2010; 21:341:c6945.
Pandian Z, Marjoribanks J, Ozturk O, Serour G, Bhattacharya S. Number of embryos for transfer following in vitro fertilisation or intra-cytoplasmic sperm injection. Cochrane Database Syst Rev. 2013; 29; 7:CD003416.
Pasquier et al. Thromb Haemost 2005.
Wang et al., Journal of Reproduction and Contraception, 2008.

The invention claimed is:

1. A method for promoting pregnancy in a mammal undergoing embryo transfer comprising culturing embryos in a culture medium, collecting the culture medium after at least one day of embryo culture, measuring the quantity of soluble CD146 (sCD146) protein in the collected culture medium, and transferring to said mammal one or more embryos collected from culture medium in which the measured quantity of sCD146 is equal to or below a threshold value.

2. The method of claim 1, said method comprising a step of examining the cultured embryos using morphological criteria and transferring at least one embryo that satisfies morphological criteria of implantation into the uterus of said mammal.

3. The method of claim 1, wherein the quantity of soluble CD146 is measured between two and five days after in vitro oocyte fertilization.

* * * * *

UNITED STATES PATENT AND TRADEMARK OFFICE
CERTIFICATE OF CORRECTION

PATENT NO. : 10,809,269 B2
APPLICATION NO. : 15/568097
DATED : October 20, 2020
INVENTOR(S) : Nathalie Bardin et al.

Page 1 of 1

It is certified that error appears in the above-identified patent and that said Letters Patent is hereby corrected as shown below:

In the Specification

Column 4,
Line 24, "600 of the" should read --600 µL, of the--.

Column 8,
Line 52, "200 of" should read --200 µL of--.

Signed and Sealed this
Sixteenth Day of March, 2021

Drew Hirshfeld
*Performing the Functions and Duties of the
Under Secretary of Commerce for Intellectual Property and
Director of the United States Patent and Trademark Office*